(12) United States Patent
Huang et al.

(10) Patent No.: US 8,073,192 B2
(45) Date of Patent: Dec. 6, 2011

(54) DETERMINING WOOD CHARACTERISTICS USING ANNUAL RING IMAGES FROM LUMBER FACES

(75) Inventors: Chih-Lin Huang, Bellevue, WA (US); Greg J Leaf, Graham, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 589 days.

(21) Appl. No.: 12/344,078

(22) Filed: Dec. 24, 2008

(65) Prior Publication Data

US 2010/0158309 A1   Jun. 24, 2010

(51) Int. Cl.
    *G06K 9/00* (2006.01)
    *G01N 21/89* (2006.01)
(52) U.S. Cl. .................................. 382/100; 250/559.25
(58) Field of Classification Search .................. None
    See application file for complete search history.

(56) References Cited

U.S. PATENT DOCUMENTS

| 4,817,021 | A | 3/1989 | Sowerby |
| 7,068,050 | B2 | 6/2006 | Steele |
| 2002/0085093 | A1* | 7/2002 | Frigon et al. ................... 348/91 |
| 2005/0013472 | A1* | 1/2005 | Gauthier ........................ 382/141 |
| 2005/0031158 | A1* | 2/2005 | Biernacki et al. ............. 382/100 |
| 2005/0190958 | A1* | 9/2005 | Woods et al. .................. 382/141 |
| 2007/0233393 | A1 | 10/2007 | Floyd |
| 2008/0140248 | A1 | 6/2008 | Moore |

OTHER PUBLICATIONS

Park et al., "Measuring maximum latewood density by image analysis at the cellular level", Wood and Fiber Science, Society of Wood Science & Technology Materials Science, Engineering, Agriculture, Ecology and Forestry, vol. 25, No. 4 / Oct. 1993 pp. 326-332. Retrieved by STIC.*
Brännström, M., et al., "Predicting Board Strength by X-Ray Scanning of Logs: The Impact of Different Measurement Concepts," Scandinavian Journal of Forest Research 22(1):60-70, 2007.
Jozsa, L.A., and G.R. Middleton, "A Discussion of Wood Quality Attributes and Their Practical Implications," Special Publication No. SP-34, Forintek Canada Corp., Vancouver, B.C., Canada, Dec. 1994.
Rozenberg, P., et al., "Improving Models of Wood Density by Including Genetic Effects: A Case Study in Douglas-Fir," Annals of Forest Science 58(4):385-394, May-Jun. 2001.
Silvennoinen, R., et al., "Detection of Wood Density by Using a DOE Sensor," Wood Science and Technology 36(2):157-162, 2002.

* cited by examiner

*Primary Examiner* — Bhavesh Mehta
*Assistant Examiner* — Tahmina Ansari
(74) *Attorney, Agent, or Firm* — Christensen O'Connor; Johnson Kindness PLLC

(57) ABSTRACT

Methods are described for predicting the percentage of latewood and specific gravity of lumber independent of moisture content using image analysis of the lumber surfaces.

20 Claims, 6 Drawing Sheets

DETERMINING WOOD CHARACTERISTICS USING ANNUAL RING IMAGES FROM LUMBER FACES

TECHNICAL FIELD

The present disclosure generally relates to methods for determining latewood percentage and specific gravity of a piece of green or dry lumber.

BACKGROUND

The specific gravity of a material is the ratio of its density to the density of pure water at 4° C. In the wood products industry, the specific gravity (or basic density) of wood is a characteristic that has implications throughout the processing of a cut tree into lumber or other wood products. The basic density of wood is based on oven-dried weight, and is related to the strength, modulus of elasticity (MOE), and pulp yield of the wood, as well as the susceptibility of the wood to uptake additives for treatment and other qualities known to those of skill in the art.

At the beginning of the processing of a tree into a wood product (e.g., lumber), the felled trees are loaded as logs onto trucks. Because all logs are not identical in composition, they are purchased based on a number of factors, including the size, shape, and weight of the logs.

Regarding tree-to-tree variation in wood characteristics, differences are typically found in the moisture content of logs on a single truck depending on the age of the trees and the freshness of the logs. There can be a 5 to 8% difference in moisture content between logs felled in the morning or in the afternoon from the same tree stand. The oven-dry-weight-based moisture content of a log can be from 50% to 200%, a wide range that leads to difficulties when processing the logs (e.g., at a lumber mill), as will be described below. Moisture content and, to a lesser extent, specific gravity can be estimated at the truck level, log level, and lumber level, but the two values are usually inextricably linked by the measurement technique, and typically no correction is made for specific gravity effects on the moisture content or vice versa.

Traditional methods for measuring moisture content include non-contact capacitance measurements and post-processing weight comparisons of pre- and post-oven-dried wood specimens. Techniques for deriving moisture content from non-contact sensors are often influenced by specific gravity, and corrections for specific gravity differences are not typically performed during wood processing.

Growth rate or rings per inch estimated from lumber end faces are used to predict several lumber properties, including specific gravity and moisture content. However, using rings per inch to measure specific gravity suffers from accuracy problems, particularly if the lumber originates from trees of uniform age (e.g., plantation-grown trees) because the end-face rings-per-inch measurement of such trees are typically homogeneous, leading to a lack of variation in estimated characteristics, even though there is likely variation in certain properties (e.g. specific gravity). Without discernable variations between logs, batching of logs based on characteristics, such as specific gravity, is difficult.

During lumber processing, lumber is transported in both linear (high speed) and transverse (low speed) processes. In traditional processing, the rings per inch observed at lumber ends are evaluated during low-speed transverse transport. Within-lumber variations of specific gravity can be very large, so a specific gravity determined based on a rings per inch measurement at the lumber end face may not be representative of the specific gravity of the entire lumber piece.

Other specific gravity (or basic density) measurement techniques include weighing, x-ray, and gamma ray techniques, all of which are complex, expensive, and affected by moisture content. The density measurement in a mill environment is usually based on as-is weight without normalizing moisture content. The effect of moisture content on the specific gravity measurement can be adjusted using a moisture content determined using a moisture meter. However, most moisture meters are accurate only within a 30% range (e.g., 5% to 35%) and report null values for moisture contents outside the range. Thus, when the moisture content of the lumber lies outside this range, such types of moisture meters do not provide moisture content measurements that should be relied upon to adjust specific gravity measurements.

The sorting of wood by specific gravity is desirable during processing of logs into lumber because wood having similar specific gravity should be similarly processed (e.g., dried at a similar rate and time to produce uniformly dried lumber). Variations in specific gravity from board to board during the lumber drying process can cause some boards to become over dried and some to be under dried, which leads to inconsistencies in the properties and shape of the dried lumber and severe drops in value of the lumber.

Additionally, the specific gravity distribution within a particular piece of lumber partially determines the amount of additives that can be absorbed into the wood during a treatment process. Under-treated lumber will be downgraded and over-treated lumber costs more to treat due to the expense of chemicals, handling, and transportation. Thus, knowledge of the distribution of specific gravity of boards, lumber, and other wood products allows for grouping of similar types of material into a batch for treatment, which will yield more uniformly treated products.

The determination of specific gravity independent of moisture content has several other advantages when processing wood products. First, the shrinkage properties of wood vary depending on the specific gravity of the wood (e.g., high specific gravity wood tends to shrink more in the transverse direction than the longitudinal direction, and low specific gravity wood tends to shrink more in the longitudinal direction than the transverse direction). Adjustments to lumber dimensions during processing can be made based on the specific gravity of the wood so as to produce uniformly dimensioned lumber across different specific gravity ranges.

A second benefit of specific gravity determination is that the commonly used capacitance method for determining moisture content can be corrected using specific gravity if such a value is known at the time of capacitance measuring. Most commercially available capacitance-based moisture content sensors includes a correction for specific gravity, yet such a correction is not typically used because the moisture content is measured early in the wood processing and the specific gravity is not then known to any level of accuracy.

A simplified method for measuring the specific gravity of wood independent from the moisture content of the wood would provide several advantages to the wood-processing industry.

SUMMARY

Methods are provided for measuring the percentage of latewood and specific gravity of lumber independent of moisture content. In one aspect, a method is provided for determining latewood percentage of at least a first portion of a piece of lumber. In one embodiment, the method includes the steps of acquiring an image of each longitudinal face of the first portion of the piece of lumber, the first portion of the piece of lumber located a first distance from a first end face of the piece of lumber, the acquired images defining a plurality of first portion images of the piece of lumber; analyzing the first portion images to determine the longitudinal face of the first portion of the piece of lumber having the highest linear density of latewood bands; and predicting the latewood percentage of the first portion of the piece of lumber using the first portion image of the longitudinal face of the first portion of the piece of lumber having the highest linear density of latewood bands.

In another aspect, a method is provided for determining the specific gravity of at least a first portion of a piece of lumber. In one embodiment, the method includes the steps of acquiring an image of each longitudinal face of the first portion of the piece of lumber, the first portion of the piece of lumber located a first distance from a first end face of the piece of lumber, the acquired images defining a plurality of first portion images of the piece of lumber; analyzing the first portion images to determine the longitudinal face of the first portion of the piece of lumber having the highest linear density of latewood bands predicting the latewood percentage of the first portion of the piece of lumber using the first portion image of the longitudinal face of the first portion of the piece of lumber having the highest linear density of latewood bands; and predicting the specific gravity of the first portion of the piece of lumber based on a determined relationship between latewood percentage and specific gravity of the first portion of the piece of lumber.

DESCRIPTION OF THE DRAWINGS

The foregoing aspects and many of the attendant advantages of the subject matter described herein will become more readily appreciated as the same become better understood by reference to the following detailed description, when taken in conjunction with the accompanying drawings, wherein.

DETAILED DESCRIPTION

Figure 1:
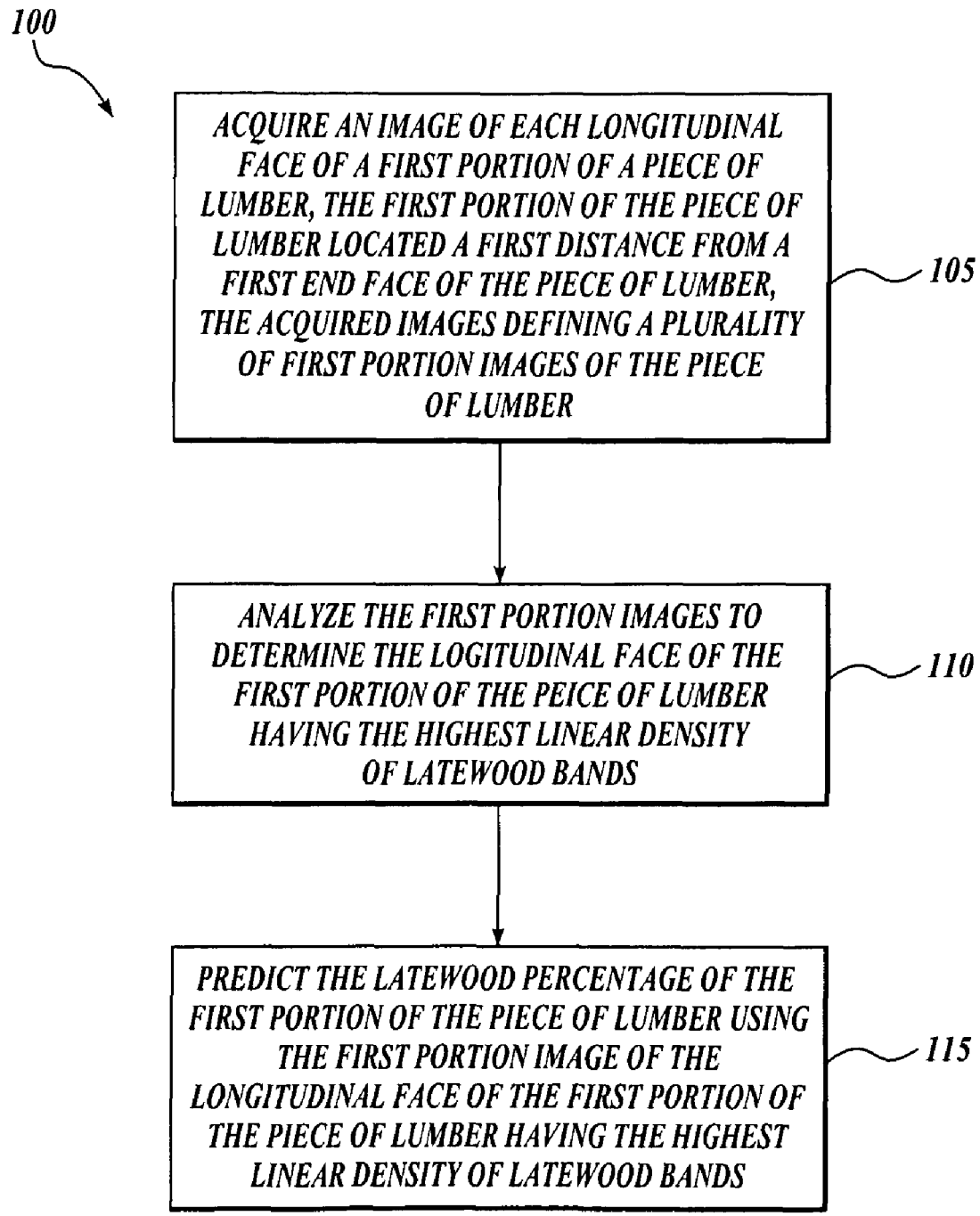
FIG. 1 is a block diagram representing a process flow of a representative method for determining latewood percentage of a portion of a piece of lumber in accordance with the embodiments described herein.

Methods are provided for measuring the percentage of latewood and specific gravity of lumber independent of moisture content. The annual rings of a tree include rings of latewood, a relatively dense wood formed near the end of the annual growing season, and earlywood, a relatively light wood formed prior to the latewood during the growing season. The methods disclosed herein utilize image analysis of the surface of a piece of lumber to predict latewood percentage. In a preferred embodiment, a cross-sectional portion is imaged on each longitudinal side of the piece of lumber and the latewood percentage of the imaged portion is predicted. Additional portions can be imaged and their latewood percentage predicted. The latewood percentage of the entire piece of lumber can be predicted by a single portion latewood percentage prediction, or by averaging the predicted latewood percentage of a plurality of portions.

The methods further utilize a correlation between latewood percentage and specific gravity to predict the specific gravity for a particular piece of lumber.

Briefly describing the methods disclosed herein, a portion of a piece of lumber is imaged on each longitudinal face by an imaging system, which generates a number of images of the surface of the portion equal to the number of longitudinal sides of the lumber. The images of the surface of the portion are then analyzed to determine which image, and thus portion surface, has the highest linear density of latewood rings. The image of the portion surface having the highest linear density of latewood rings is then analyzed to determine the percentage of the image occupied by latewood rings. The latewood percentage of the selected portion surface is predictive of the latewood percentage of the entire cross-sectional portion. Any number of additional cross-sectional portions can be similarly analyzed to predict the latewood percentages of the additional portions. In one embodiment, the average of the predicted latewood percentages of all cross-sectional portions along the length of the piece of lumber is used to predict the latewood percentage of the entire piece of lumber. In a further aspect, the latewood percentages of the cross-sectional portions of the piece of lumber are then used to predict the specific gravity of the piece of lumber using a determined relationship.

A representative method occurs in a wood processing facility, such as a lumber mill, where it is desirable to sort a cut piece of lumber (also referred to herein as a "board") based on a characteristic related to the latewood percentage of the piece of lumber (e.g., specific gravity). Lumber useful in the methods can be lumber to be cut to both standard sizes (e.g., 2×4, 2×6, 4×4, etc.) and nonstandard sizes, including lumber with more or less than four longitudinal faces. Lumber in a traditional mill is transported through processing steps on a conveyance system linearly or transversely.

The methods disclosed herein provide the advantageous capability to predict the latewood percentage and specific gravity of a piece of lumber at any longitudinal position (referred to herein as a "cross-sectional portion" or "portion") along the length of a board. Additionally, multiple portions of a board (or a continuous scan) can be measured and an average latewood percentage and specific gravity for the entire board can be predicted. Because latewood percentage and specific gravity vary along the length of a board, the methods disclosed herein provide for more accurate measurement of whole-board latewood percentage and specific gravity than an end-face measurement would. A determination of the average latewood percentage and specific gravity of the board can then be used to batch the board based on latewood percentage and/or specific gravity for further processing.

The methods will now be described in greater detail with reference to FIGS. 1-6.

Referring now to FIG. 1, a method 100 for predicting latewood percentage of at least a portion of a piece of lumber is illustrated by a flow chart.

The method 100 begins with a step 105 of acquiring an image of each longitudinal face of a first portion of a piece of lumber, the first portion of the piece of lumber located a first distance from a first end face of the piece of lumber, the acquired images defining a plurality of first portion images of the piece of lumber. Acquiring the portion images is accomplished using one or more cameras to image each longitudinal face of the piece of lumber. In one embodiment, the image acquisition in step 105 results in a number of portion images equal to the number of faces of the piece of lumber being analyzed (typically four faces). The portion image of each longitudinal face is acquired at a similar distance from an end face of the lumber such that a composite of all portion images acquired for a particular piece of lumber yields a wrap-around image of the cross-sectional portion that captures the surface images of each face of the lumber at a consistent distance along the length of the board.

The dimensions of the portion images are defined partially by the dimensions of the lumber. Because the portion images cover the width of the board face imaged, the width of the image is substantially equal to the width of the imaged board face. Thus, in a representative example, imaging a nominal 2×4 board will yield two 1.5" wide images and two 3.5" images. The height of the portion images is large enough to allow for distinction between earlywood and latewood in the images, and can be as small as a single row of pixels of a camera or the diffused image of a laser line.

The method 100 continues with a step 110 of analyzing the first portion images to determine the longitudinal face of the first portion of the piece of lumber having the highest linear density of latewood bands. The portion images acquired in step 105 are analyzed in step 110 using either a one-dimensional or two-dimensional analysis of the portion images to determine the linear density of latewood bands present in each image.

In a representative embodiment, a one-dimensional analysis is used, wherein a single analysis line (e.g., line of pixels) drawn normal to the cut longitudinal edge of the lumber (i.e., a latitudinal line) of the image from each portion image is analyzed. An analysis of the image along the analysis line typically sorts the pixels of the portion image into either latewood (darker) and earlywood (lighter) portions based on thresholding techniques known to those of skill in the art of image analysis. For example, different lighting and staining methods can be used to improve the quality of the acquired images. The boundaries between earlywood and latewood can be improved using edge enhancing routines, and because the latewood tracheids tend to generate elongated diffuse light patterns, a laser line can be shined on the lumber surface to enhance the contrast between earlywood and latewood (i.e., via the tracheid effect). Methods for analyzing wood using the tracheid effect are described in U.S. Pat. No. 7,304, 740, incorporated herein by reference in its entirety.

A representative measurement for linear density is the number of latewood bands per unit measure, such as latewood bands per inch.

After determining the linear density of latewood bands in each portion image, the portion image having the highest linear density of latewood is determined. The portion image having the highest linear density of latewood is used for further steps (e.g., 115) of the method 100.

The method 100 concludes with a step 115 of predicting the latewood percentage of the first portion of the piece of lumber using the first portion image of the longitudinal face of the first portion of the piece of lumber having the highest linear density of latewood bands. According to the methods disclosed herein, the latewood percentage of the portion is predicted based upon a determination of the percentage of the portion image (of the longitudinal face of the piece of lumber having the highest linear density of latewood bands) that represents latewood bands. The percentage of the portion image that represents latewood bands can be determined using imaging techniques known to those of skill in the art, including thresholding pixel analysis.

The portion image having the highest linear density of latewood bands is used to predict the latewood percentage of the entire cross-section of the portion using the assumption that the percentage of latewood in the portion image is equal to the percentage of latewood in the entire cross-section of the portion of the piece of lumber.

In a similar manner, the latewood percentage of the entire piece of lumber can be predicted by using the latewood percentage predicted for a single portion, as described above, or by averaging the latewood percentages predicted for a plurality of portions (each having a latewood percentage predicted using the above method) along the length of the piece of lumber.

Additionally, because latewood percentage can be predicted at several portions along the length of the piece of lumber, a map of latewood percentage variation can be generated. Such a mapping of latewood percentage (and, optionally, specific gravity) can be used to determine the quality of the wood of the piece of lumber because uniformity in wood density in a board leads to a more valuable product.

The method 100 provides an estimate of latewood percentage of a portion or entire piece of lumber using imaging techniques and equipment capable of deployment in wood processing facilities. Additionally, the method 100 can be performed as an aspect of a high-speed linear processing line (e.g., in a lumber mill), where analysis can be performed as quickly as lumber can be moved past the image acquisition hardware (such as cameras).

In one embodiment, the image acquisition system includes one or more cameras operating at visible wavelengths of light.

Figure 2A:
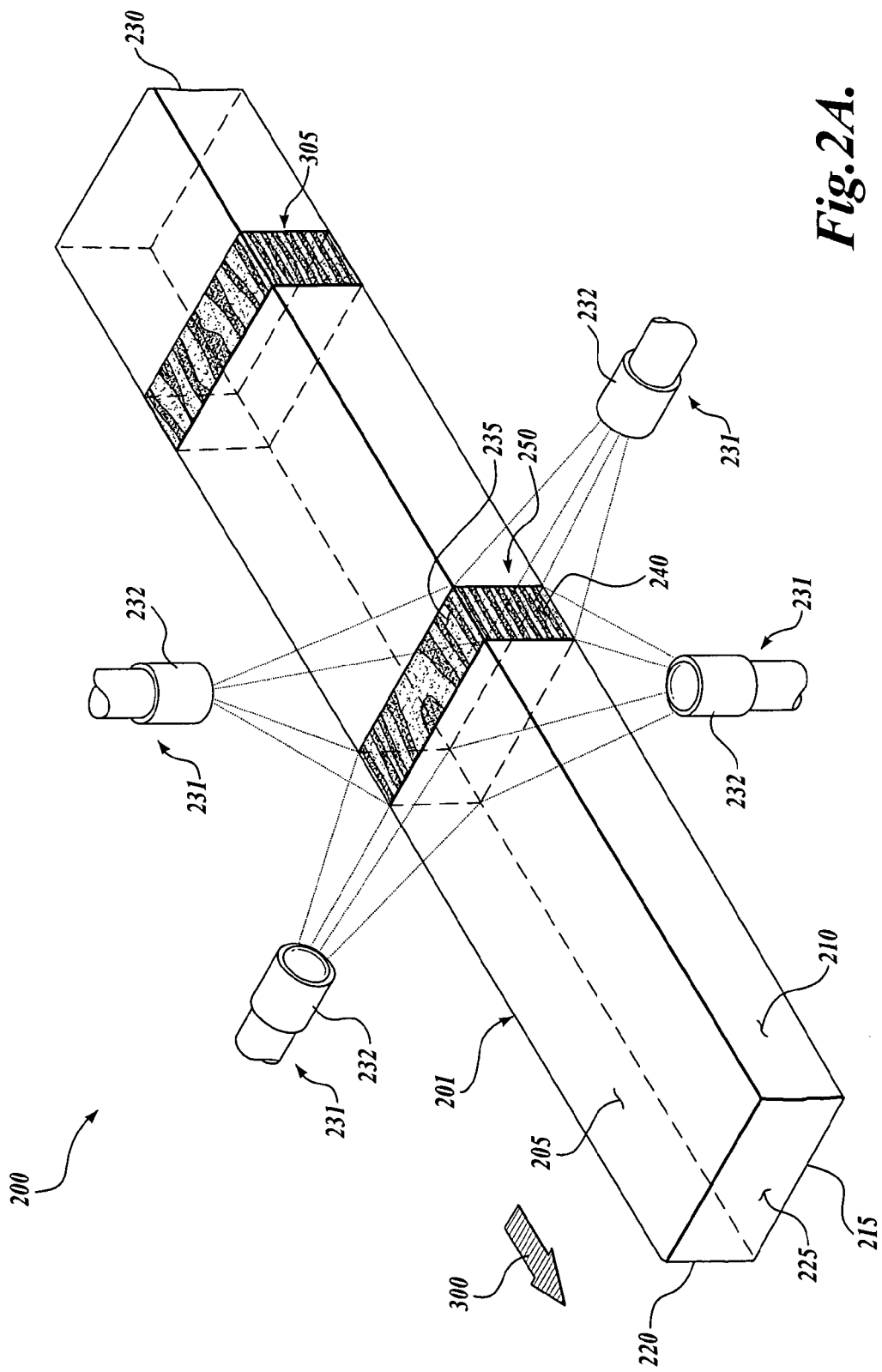
FIG. 2A is a perspective diagrammatic view of a piece of lumber imaged using an imaging system to generate an image of a portion of the longitudinal faces of the lumber in accordance with the embodiments described herein.

The method 100 provided herein and described with reference to FIG. 1 may be more readily understood by the following description made with reference to FIGS. 2A and 2B. FIG. 2A is a perspective illustration of an exemplary system for performing the methods provided herein. Referring now to FIG. 2A, a system 200 useful for performing the method 100 is illustrated. The system 200 receives a piece of lumber 201 having a top side 205, a right side 210, a bottom side 215, and a left side 220. The lumber 201 also includes a near end face 225 and a far end face 230. The lumber 201 is imaged by an imaging system 231 that includes, in this representative illustration, a plurality of cameras 232. The imaging system 23f also includes a number of elements not illustrated, including devices, such as a computer, capable of controlling the cameras 232 and for receiving and analyzing the images captured by the cameras 232. Optionally, the system 231 includes a lighting system capable of enhancing the contrast between early wood and latewood bands.

In operation, the imaging system 231 captures images of a cross-sectional portion 250 of each longitudinal face (e.g. 205, 210, 215, and 220) at a similar distance from an end face (e.g., 225 and 230) of the piece of lumber 201. The resulting portion images (235 and 240 illustrated in FIG. 2A; and 241 and 242, illustrated in FIG. 2B) captured by the imaging system 231 include the latewood and earlywood bands of the surface of the lumber 201. The portion images 235, 240, 241, and 242 captured by the imaging system 231 are used in the methods provided herein to predict latewood percentage of the portion of the piece of lumber 201.

The latewood bands (dark bands) are illustrated in FIG. 2A only in the region of the piece of lumber 201 where the portion images 235, 240 are acquired. It will be appreciated that the confinement of the latewood bands to the portion images 235, 240 is for illustrative effect only, and that the latewood bands of an actual piece of lumber 201 occur across the entire surface of the piece of lumber 201.

In an exemplary embodiment, the piece of lumber 201 is moved in relation to the imaging system 231 in the direction of arrow 300 such that a second cross-sectional portion 305 can be imaged by the imaging system 231. Imaging and analysis for latewood percentage of the second cross-sectional portion 305 is accomplished using the methods provided herein as described with reference to cross-sectional portion 250. The latewood percentage (and specific gravity) of the entire piece of lumber 201 can be predicted using image analysis of a single cross-sectional portion (e.g., 250), or by analyzing multiple cross-sectional portions (e.g., 250 and 305).

The exemplary system 200 described with reference to FIG. 2A can be integrated into a wood-processing facility where the lumber 201 is transported past the imaging system 231 on a mechanical conveyance (not pictured).

Figure 2B:
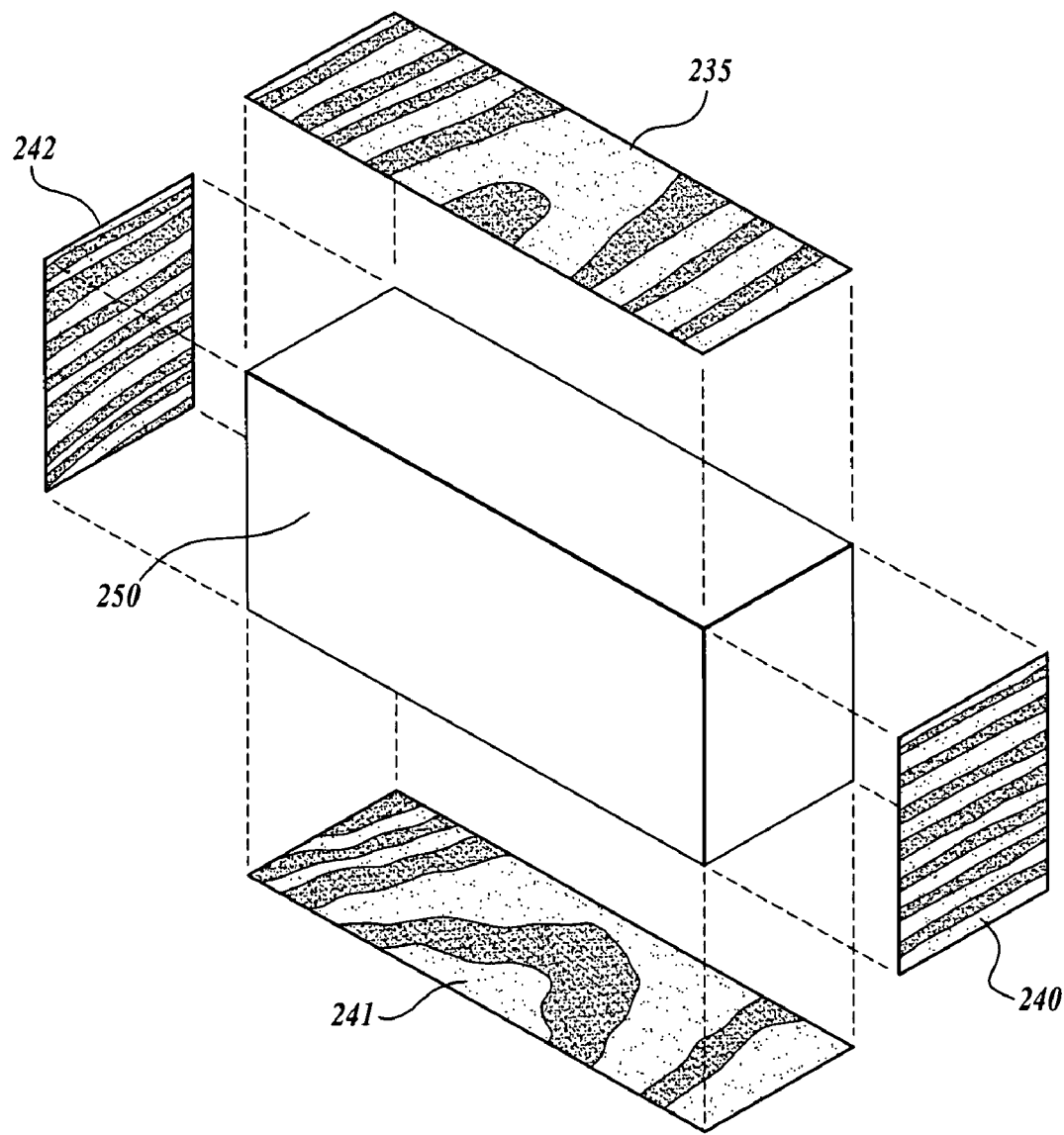
FIG. 2B is an exploded view of a portion of FIG. 2A illustrating the images of four longitudinal faces of the portion of the piece of lumber generated by the imaging system.

Referring now to FIG. 2B, an exploded view of the cross-sectional portion 250 of FIG. 2A is illustrated. In FIG. 2B, four portion images 235, 240, 241, and 242 are illustrated removed from the surface of the cross-sectional portion 250 so that all four portion images 235, 240, 241, and 242 are viewable. As a result of the exploded view of FIG. 2B, the portion images 241 and 242 are illustrated from the bottom side of the image (i.e., the images illustrate faces of the cross-sectional portion 250). The top-side images of portion images 241 and 242 are acquired and used in the method.

Figure 3:
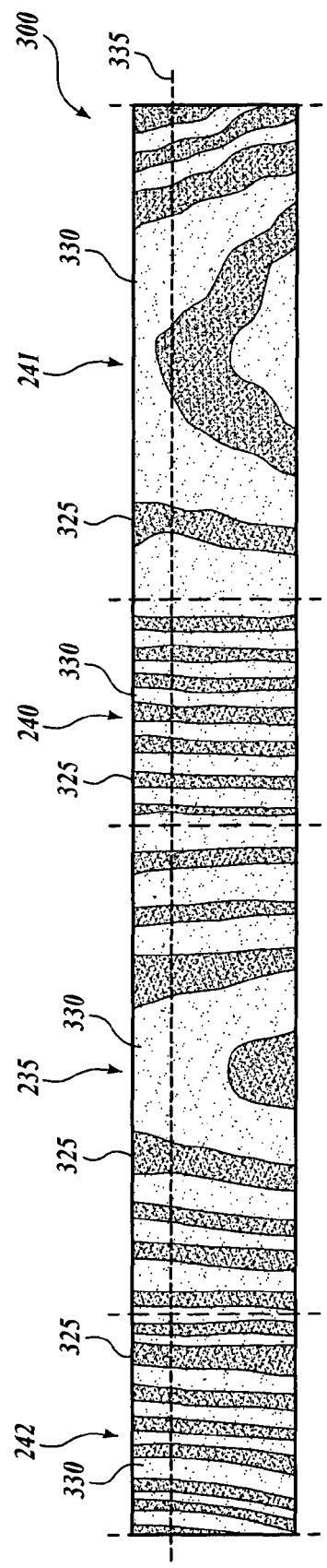
FIG. 3 is an illustration of a composite portion image of the piece of lumber illustrated in FIGS. 2A and 2B.

Referring now to FIG. 3, a composite image 300 of portion images 235, 240, 241, and 242 acquired from the cross-sectional portion 250 of the piece of lumber 201 is illustrated. FIG. 3 illustrates latewood bands 325 and the earlywood bands 330 separating the latewood bands 325. The number of latewood bands 325 can be calculated based on image analysis.

A representative technique for determining the number of latewood bands 325 in a portion image (e.g. 235) utilizes a threshold brightness value to distinguish between latewood (dark) and earlywood (light). If a pixel in a portion image 235 is brighter than the threshold brightness then the wood surface represented by that pixel is determined to be earlywood; conversely, if the pixel is darker than the threshold brightness then the wood is determined to be latewood. Such a determination of brightness values in an image is typically performed using a computer enabled with the appropriate image-analysis software. A lighting system (e.g., a laser system) can be used to improve the contrast between the earlywood and latewood so as to improve the accuracy of the thresholding.

The portion image 235, 240, 241, or 242 having the highest linear density of latewood bands 325 is selected for further analysis to predict the latewood percentage of the portion 250 or entire piece of lumber 201.

In the exemplary composite image 300 illustrated in FIG. 3, portion 242 has eight latewood bands 325 and, thus, would likely be selected as the portion image having the highest linear density of latewood bands.

In a representative embodiment, a linear section of the composite image 300 or portion images 235, 240, 241, and 242 is analyzed for latewood bands 325. In an exemplary embodiment described with reference to FIG. 3, only an analysis line 335 is used to analyze the composite image 300 for latewood bands 325 instead of the entire composite image 300.

Figure 4:
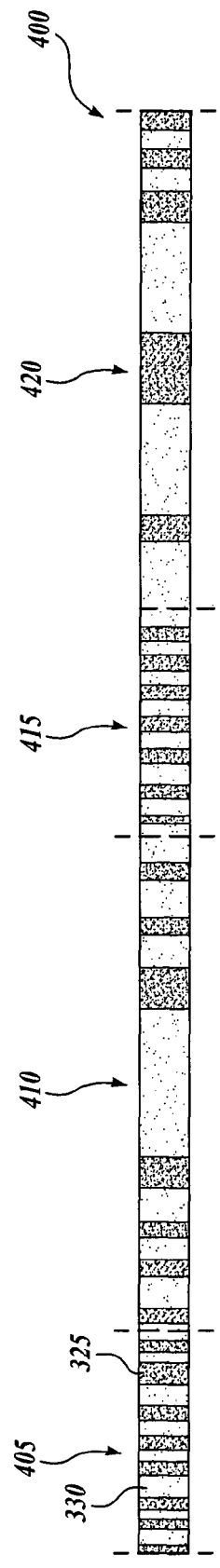
FIG. 4 is an illustration of a line scan image taken from the composite portion image illustrated in FIG. 3.

Referring now to FIG. 4, a substantially one-dimensional linear section image 400 (made slightly two-dimensional for ease of viewing) representing the composite image 300 along only the analysis line 335 is illustrated. Light areas represent earlywood 330, while dark areas represent latewood 325. The portion images 235, 240, 241, 242 from FIG. 3 are reduced to linear portions 405, 410, 415, 425 in FIG. 4, with linear portion 405 corresponding to portion 242, linear portion 410 corresponding to portion 235, linear portion 415 corresponding to portion 240, and linear portion 420 corresponding to portion 241.

In this exemplary embodiment, as determined with reference to FIG. 3, portion 242 (and, thus, linear portion 405) have the highest linear density of latewood bands 325 in the portion images 300, 400, and is used to predict the overall latewood percentage of the portion of the piece of lumber 201. In this exemplary embodiment, image analysis of linear portion 405 is used to determine the percentage of latewood in the portion 405. This latewood percentage in the portion 405 is determined to be equal to the latewood percentage of the entire cross-sectional portion 250.

A representative technique for determining the percentage of a portion image (e.g. 235 or 410) that represents latewood bands utilizes a threshold brightness value to distinguish between latewood (dark) and earlywood (light). If a pixel in a portion image is brighter than the threshold brightness then the wood surface represented by that pixel is determined to be earlywood; conversely, if the pixel is darker than the threshold brightness then the wood is determined to be latewood. The relative number of dark pixels to light pixels can be used to determine the percentage of the portion image that represents latewood bands which is used as a prediction of the latewood percentage for the portion of lumber imaged. Such a determination of brightness values in an image is typically performed using a computer enabled with the appropriate image-analysis software.

Figure 5:
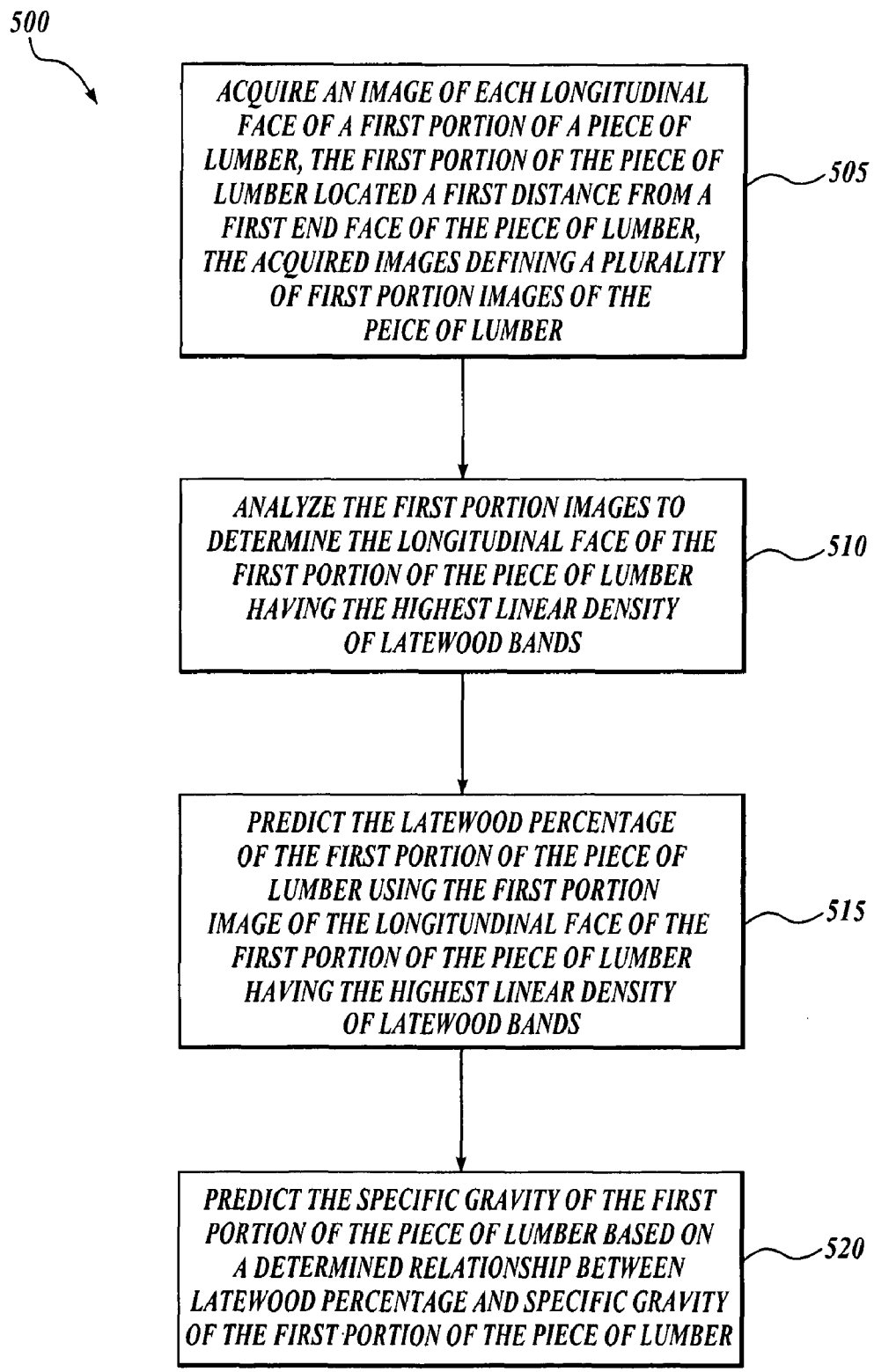
FIG. 5 is a block diagram representing a process flow of a representative method for determining the specific gravity of a portion of a piece of lumber in accordance with the embodiments described herein.

In one aspect, a method is provided for determining the specific gravity of lumber. The specific gravity determination method provided herein is a variation on the previously described (with reference to FIGS. 1-4) method 100 for determining the latewood percentage of a piece of lumber. Referring now to FIG. 5, the specific gravity determination method will now be described.

The method 500 begins with a step 505 of acquiring an image of each longitudinal face of a first portion of a piece of lumber, the first portion of the piece of lumber located a first distance from a first end face of the piece of lumber, the acquired images defining a plurality of first portion images of the piece of lumber.

The method 500 continues with a step 510 of analyzing the first portion images to determine the longitudinal face of the first portion of the piece of lumber having the highest linear density of latewood bands, as described above with reference to FIG. 3.

The method 500 continues with a step 515 of predicting the latewood percentage of the first portion of the piece of lumber using the first portion image of the longitudinal face of the first portion of the piece of lumber having the highest linear density of latewood bands, as described above with reference to FIG. 4.

The method 500 concludes with a step 520 of predicting the specific gravity of the first portion of the piece of lumber based on a determined relationship between latewood percentage and specific gravity of the first portion of the piece of lumber. A representative method for determining a relationship between latewood percentage and specific gravity includes the use of known specific gravity values for both latewood and earlywood. A second representative method for determining the relationship between latewood percentage and specific gravity includes correlating latewood percentage to specific gravity to create a calibration upon which specific gravity can be predicted for any latewood percentage. The calibration method is most effective when applied to a particular species and type of wood, and is most effective when applied to similar-aged wood, wood from logs harvested in a similar area, and wood cut from similar parts of a tree (e.g., butt logs and tops or heartwood and sapwood). The intended use of the calibration information and the speed of the wood processing systems are also factors when designing a calibration process.

Figure 6:
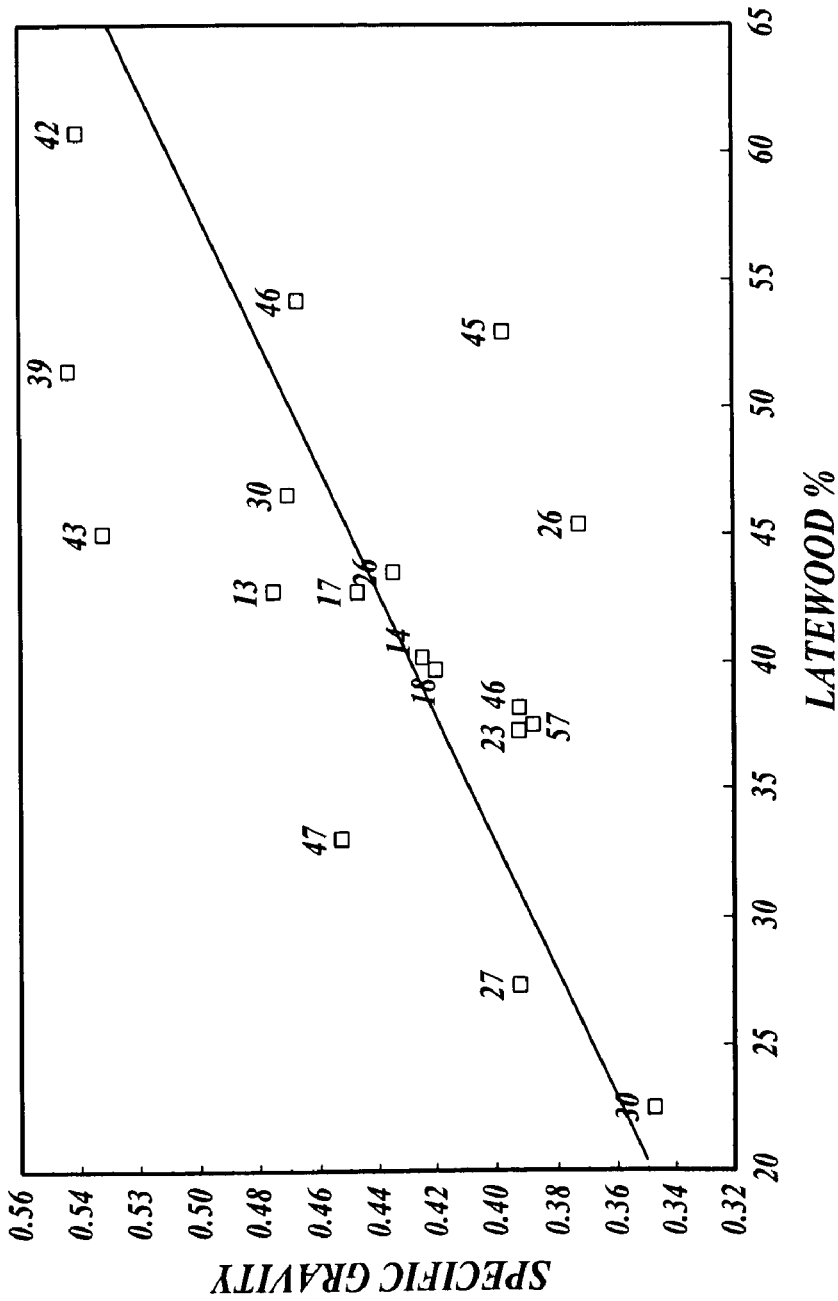
FIG. 6 is an x-y scatter plot illustrating a latewood percentage versus specific gravity correlation, as is useful in embodiments described herein.

FIG. 6 is a graph illustrating a calibration between the latewood percentages of 6" portions of 2×4 lumber pieces cut from green lumber at a mill in North Carolina. The specific gravity of each segment was determined by oven dry weight and known volume. The number-labeled data points in the x-y scatter graph represent individual portions tested to generate the figure, and the line drawn through the diagonal of the figure represents a line of best fit for the data.

A calibration, such as that illustrated in FIG. 6, can be applied to predict the specific gravity of a piece of lumber. The latewood percentage is first predicted, using the methods described herein. Based on the predicted latewood percentage for the piece of lumber, the specific gravity of the piece of lumber is predicted using the graph of FIG. 6. For example, a latewood percentage of 35%, determined by image analysis, would correlate to a specific gravity of 0.41 according to the graph of FIG. 6.

The specific gravity predicted using the provided method is useful to one of skill in the art to determine the proper treatment, strength grading, moisture-meter correction, and processing condition (e.g., drying) for a particular piece of green or dry lumber. The implementation of the method into a lumber mill or similar processing environment can be used to optimize the processes implemented and the products produced based on the predicted specific gravity of the lumber being processed, including both an average specific gravity for an entire board, or a map of variations in specific gravity throughout the board.

While illustrative embodiments have been illustrated and described, it will be appreciated that various changes can be made therein without departing from the spirit and scope of the invention. Aspects of the disclosure described in the context of particular embodiments may be combined or eliminated in other embodiments.

Further, while advantages associated with certain embodiments of the disclosure may have been described in the context of those embodiments, other embodiments may also exhibit such advantages, and not all embodiments need necessarily exhibit such advantages to fall within the scope of the disclosure. Accordingly, the invention is not limited except as by the appended claims.

We claim:

1. A method for determining latewood percentage of at least a first portion of a piece of lumber comprising the steps of:
   (a) acquiring an image of each longitudinal face of the first portion of the piece of lumber, the first portion of the piece of lumber located a first distance from a first end face of the piece of lumber, the acquired images defining a plurality of first portion images of the piece of lumber;
   (b) analyzing the first portion images to determine the longitudinal face of the first portion of the piece of lumber having the highest linear density of latewood bands; and
   (c) predicting the latewood percentage of the first portion of the piece of lumber using the first portion image of the longitudinal face of the first portion of the piece of lumber having the highest linear density of latewood bands.

2. The method of claim 1, further comprising predicting the latewood percentage of the entire piece of lumber using the predicted latewood percentage of the first portion of the piece of lumber.

3. The method of claim 1, wherein acquiring an image of each longitudinal face of the first portion of the piece of lumber comprises conveying the piece of lumber past an imaging system.

4. The method of claim 3, wherein the imaging system comprises a plurality of cameras.

5. The method of claim 1, wherein analyzing the first portion images to determine the longitudinal face of the first portion of the piece of lumber having the highest linear density of latewood bands comprises determining the number of latewood bands per inch of each first portion image.

6. The method of claim 1, wherein predicting the latewood percentage of the first portion of the piece of lumber using the first portion image of the longitudinal face of the first portion of the piece of lumber having the highest linear density of latewood bands comprises determining the percentage of the first portion image having the highest linear density of latewood bands that represents latewood bands.

7. The method of claim 6, wherein determining the percentage of the first portion image that represents latewood bands comprises defining a threshold brightness value and determining the percentage of the first portion image having a measured brightness lower than the threshold brightness value.

8. The method of claim 1, wherein the method further comprises the steps of:
   (d) acquiring an image of each longitudinal face of a second portion of the piece of lumber at a second distance from the first end face of the piece of lumber, the second distance being different from the first distance, the acquired images of the second portion defining a plurality of second portion images of the piece of lumber;
   (e) analyzing the second portion images to determine the longitudinal face of the second portion of the piece of lumber having the highest linear density of latewood bands; and
   (f) predicting the latewood percentage of the second portion of the piece of lumber using the second portion image of the longitudinal face of the second portion of the piece of lumber having the highest linear density of latewood bands.

9. The method of claim 8, further comprising predicting the latewood percentage of the entire piece of lumber using at least the first portion image of the longitudinal face of the first portion of the piece of lumber having the highest linear density of latewood bands and the second portion image of the longitudinal face of the second portion of the piece of lumber having the highest linear density of latewood bands.

10. The method of claim 9, further comprising predicting the latewood percentage of the entire piece of lumber using at least the latewood percentage predicted from the first portion images and the second portion images.

11. A method for determining the specific gravity of at least a first portion of a piece of lumber comprising the steps of:

(a) acquiring an image of each longitudinal face of the first portion of the piece of lumber, the first portion of the piece of lumber located a first distance from a first end face of the piece of lumber, the acquired images defining a plurality of first portion images of the piece of lumber;
(b) analyzing the first portion images to determine the longitudinal face of the first portion of the piece of lumber having the highest linear density of latewood bands;
(c) predicting the latewood percentage of the first portion of the piece of lumber using the first portion image of the longitudinal face of the first portion of the piece of lumber having the highest linear density of latewood bands; and
(d) predicting the specific gravity of the first portion of the piece of lumber based on a determined relationship between latewood percentage and specific gravity of the first portion of the piece of lumber.

12. The method of claim 11, further comprising predicting the specific gravity of the entire piece of lumber using the predicted specific gravity of the first portion of the piece of lumber.

13. The method of claim 11, wherein acquiring an image of each longitudinal face of the first portion of the piece of lumber comprises conveying the piece of lumber past an imaging system.

14. The method of claim 13, wherein the imaging system comprises a plurality of cameras.

15. The method of claim 11, wherein analyzing the first portion images to determine the longitudinal face of the first portion of the piece of lumber having the highest linear density of latewood bands comprises determining the number of latewood bands per inch of each first portion image.

16. The method of claim 11, wherein predicting the latewood percentage of the first portion of the piece of lumber using the first portion image of the longitudinal face of the first portion of the piece of lumber having the highest linear density of latewood bands comprises determining the percentage of the first portion image having the highest linear density of latewood bands that represents latewood bands.

17. The method of claim 16, wherein determining the percentage of the first portion image that represents latewood bands comprises defining a threshold brightness value and determining the percentage of the first portion image having a measured brightness lower than the threshold brightness value.

18. The method of claim 11, wherein the method further comprises the steps of:
(e) acquiring an image of each longitudinal face of a second portion of the piece of lumber at a second distance from the first end face of the piece of lumber, the second distance being different from the first distance, the acquired images of the second portion defining a plurality of second portion images of the piece of lumber;
(f) analyzing the second portion images to determine the longitudinal face of the second portion of the piece of lumber having the highest linear density of latewood bands;
(g) predicting the latewood percentage of the second portion of the piece of lumber using the second portion image of the longitudinal face of the second portion of the piece of lumber having the highest linear density of latewood bands; and
(h) predicting the specific gravity of the second portion of the piece of lumber based on a determined relationship between latewood percentage and specific gravity of the second portion of the piece of lumber.

19. The method of claim 18, further comprising predicting the specific gravity of the entire piece of lumber using at least the first portion image of the longitudinal face of the first portion of the piece of lumber having the highest linear density of latewood bands and the second portion image of the longitudinal face of the second portion of the piece of lumber having the highest linear density of latewood bands.

20. The method of claim 19, further comprising predicting the specific gravity of the entire piece of lumber using at least the specific gravity predicted from the first portion images and the second portion images.

* * * * *